United States Patent [19]
Goldberg et al.

[11] Patent Number: 6,156,315
[45] Date of Patent: Dec. 5, 2000

[54] METHOD FOR INHIBITING THE BINDING OF LOW DENSITY LIPOPROTEIN TO BLOOD VESSEL MATRIX

[75] Inventors: Ira J. Goldberg, New York, N.Y.; Sivaram Pillarisetti, Bergenfield, N.J.

[73] Assignee: The Trustees of Columbia University in the City of New York, New York, N.Y.

[21] Appl. No.: 08/966,296

[22] Filed: Nov. 7, 1997

Related U.S. Application Data

[60] Provisional application No. 60/063,468, Oct. 10, 1997.

[51] Int. Cl.$^7$ .................................................. A61K 39/395
[52] U.S. Cl. ..................................... 424/158.1; 424/139.1; 424/141.1; 424/172.1; 530/350; 530/359; 530/388.25
[58] Field of Search ............................. 424/130.1, 139.1, 424/141.1, 172.1, 158.1; 530/350, 359, 388.25

[56] References Cited

PUBLICATIONS

Corsini et al. "Monoclonal Antibody 5A Binds Apolipoprotein B–48 and Inhibits the Low–Density Li–poprotein–Receptor Interaction", Biochemical and Biophysical Research Communications, vol. 162, No. 3 (Aug. 15, 1989), pp. 908–915.

McCormick, S.P.A., et al., (1997) "Transgenic Mice Expressing Human ApoB95 and ApoB97" *J.of Bio. Chem.*, 272:23616–23622 (Exhibit 1); and.

Pang, L., Pillarisetti, S., and Goldberg, I.J., (1996) "Cell–surface Expression of an Amino–terminal Fragment of Apolopoprotein B Increases Lipoprotein Lipase Binding to Cells" *J.of Bio.Chem.* 271:19518–19523 (Exhibit 2).

Gianturco S. H., Cellular Binding Site and Membrane Binding Proteins for Triglyceride–Rich Lipoproteins in Human Monocyte–Macrophages and THP–1 Monocytic Cells (1994) J. Lip. Res. 35:1674–1687.

Gretch, D. G., The Amino Terminus of Apolipprotein B is Necessary but not Sufficient for Microsomal Triglyceride Transfer Protein Responsiveness (1996) J. Biol. Chem. 271:8682–8691.

Ingram, M. F., Folding of the Amino–Terminal Domain of Apoli–poprotein B Initiates Microsomal Triglyceride Transfer Protein–Dependent Lipid Transfer to Nascent Very Low Denisty Lipo–Protein (1997) J. Biol. Chem 272: 10279–10286.

Kruezer J., et al., Amino Terminus of Apolipoprotein B Suffices to Produce Recognition of Malondialdehye–Modified Low Density Lipoprotein by the Scavenger Receptor of Human Monocyte–Macrophages (1997) J. Lip. Res. 38: 324–342.

Rutledge J. C., et al., Lipoprotein Lipase Increases Lipo–Protein Binding to the Artery Wall and Increases Endothelial Layer Permeability by Formation of Lipolysis Products (1997) Circulation Research 80: 819–828.

Saxena U., et al., LIPOPROTEIN LIPASE INCREASES LOW DENSITY LIPOPROTEIN RETENTION BY SUB-ENDOTHELIAL CELL MATRIX (1992) J. Clin. Invest. 89: 373–380.

Shih I. L., et al., Focal Accumulation of an Apolipoprotein B–Based Synthetic Oligopeptide in the Healing of Rabbit Arterial Wall (1990) Proc. Nat'l. Acad. Sci. 87: 1436–1440.

Sivaram P., et al, An Amino–Terminal Fragment of Apolipo–protein–B Binds to Lipoprotein Lipase and May Facilitate its Protein–B Binds to Lipoprotein Lipase and May Facilitate its Binding to Endothelial Cells (1994) J. Biol. Chem. 269: 9409–9412.

Veniant M. M., et al., "Susceptibility to Atherosclerosis in Mice Expressing Exclusively Apolipoprotein B48 or Apolipo–Protein B100," (1997) J. Clin. Invest. 100: 180–188.

*Primary Examiner*—Jeffrey Stucker
*Attorney, Agent, or Firm*—John P. White; Cooper & Dunham LLP

[57] ABSTRACT

This invention also provides a method of treating atherosclerosis in a subject, comprising administering to the subject an effective amount of a substance capable of binding to the amino-terminal region of apolipoprotein B, thereby treating the atherosclerosis. This invention also provides a method for inhibiting the binding of low density lipoprotein to blood vessel matrix in a subject, comprising administering to the subject an effective amount of a substance capable of competing with the amino-terminal region of apolipoprotein B for binding to blood vessel matrix, thereby inhibiting the binding of low density lipoprotein to blood vessel matrix. This invention also provides a method for identifying a compound capable of ameliorating atherosclerosis. Additionally, this invention provides a kit for inhibiting the binding of low density lipoprotein to blood vessel matrix, wherein the kit comprises a substance capable of binding to the amino-terminal region of apolipoprotein B.

8 Claims, 9 Drawing Sheets

Figure 1

MDPPRPALLALLALPALLLLLLAGARAEEEMLENVSLVCPKDATRFKHLRKYTYNYEAESSS
GVPGTADSRSATRINCKVELEVPQLCSFILKTSQCTLKEVYGFNPEGKALLKKTKNSEEFAA
AMSRYELKLAIPEGKQVFLYPEKDEPTYILNIKRGIISALLVPPETEEAKQVLFLDTVYGNC
STHFTVKTRKGNVATEISTERDLGQCDRFKPIRTGISPLALIKGMTRPLSTLISSSQSCQYT
LDAKRKHVAEAICKEQHLFLPFSYNNKYGMVAQVTQTLKLEDTPKINSRFFGEGTKKMGLAF
ESTKSTSPPKQAEAVLKTLQELKKLTISEQNIQRANLFNKLVTELRGLSDEAVTSLLPQLIE
VSSPITLQALVQCGQPQCSTHILQWLKRVHANPLLIDVVTYLVALIPEPSAQQLREIFNMAR
DQRSRATLYALSHAVNNYHKTNPTGTQELLDIANYLMEQIQDDCTGDEDYTYLILRVIGNMG
QTMEQLTPELKSSILKCVQSTKPSLMIQKAAIQALRKMEPKDKDQEVLLQTFLDDASPGDKR
LAAYLMLMRSPSQADINKIVQILPWEQNEQVKNFVASHIANILNSEELDIQDLKKLVKEALK
ESQLPTVMDFRKFSRNYQLYKSVSLPSLDPASAKIEGNLIFDPNNYLPKESMLKTTLTAFGF
ASADLIEIGLEGKGFEPTLEALFGKQGFFPDSVNKALYWVNGQVPDGVSKVLVDHFGYTKDD
KHEQDMVNGIMLSVEKLIKDLKSKEVPEARAYLRILGEELGFASLHDLQLLGKLLLMGARTL
QGI

Figure 2

ApoB17 Has a Greater Affinity for Heparin than B100

Figure 3

ApoB48 Particles Have a Greater Affinity for Heparin than B100 Particles

B-100 (ApoB100 Tg Mouse)

ApoB48 (E Null Mouse)

Figure 4

LDL Binding to Heparin Sepharose in
the Presence of MB19 and MB47

METHOD FOR INHIBITING THE BINDING OF LOW DENSITY LIPOPROTEIN TO BLOOD VESSEL MATRIX

This application claims the benefit of U.S. Provisional application Ser. No. 60/063,468 filed Oct. 10, 1997, the content of which is incorporated into this application by reference.

The invention disclosed herein was made with Government support under NIH Grant Nos. HL 56984 and HL 45095 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains.

BACKGROUND OF THE INVENTION

Atherosclerosis is the most common cause of coronary heart disease, including angina pectoris and heart attacks. Atherosclerosis is also a major cause of strokes. Atherosclerosis is characterized by a buildup of fatty deposits, called plaques, on the inner walls of arteries and a resulting decrease in the normal flow of the blood through the artery. These plaques are made up of cholesterol and other lipids. Low density lipoproteins (LDL) are the major carriers of cholesterol in the blood and are believed to be responsible for mediating the arterial accumulation of cholesterol that causes Atherosclerosis. The subendothelial accumulation of LDL is a major atherosclerosis initiating event.

Low density lipoproteins (LDLs) are roughly spherical complexes of lipids and proteins. The predominant protein constituent of LDL is Apolipoprotein B-100 (ApoB100). L. Chan (1992) J. Biol. Chem. 267, 25621–25624. LDL represents only one of a large class of lipoproteins. Other lipoproteins, in order of increasing 5 density, include: chylomicrons, very low-density lipoprotein (VLDL), low-density lipoprotein (LDL), high- density lipoprotein (HDL), and very high-density lipoprotein (VHDL).

Several lipoproteins have also been implicated in the etiology of atherosclerosis. For example, lipoprotein lipase (LpL) has been shown to have multiple interactions with lipoproteins and components of the blood vessel wall. U. Saxena et al. (1992) J. Clin. Invest. 89, 373–380. In particular, LpL has a lipid-binding domain that binds to VLDLs and LDLs with higher affinity than high- density lipoproteins. S. Choi et al. (1995) J. Biol. Chem. 270, 8081–8086. LpL is also able to associate with proteoglycans in the subendothelial cell matrix of blood vessels. It's been shown that these interactions allow LpL to increase LDL binding to blood vessels and thereby act as an atherogenic factor. J. C. Rutledge, M. M. Woo, A. A. Rezai, L. K. Curtiss, I. J. Goldberg (1997) Circulation Research 80, 819–828.

The polypeptide components of lipoproteins are called apolipoproteins and are synthesized mainly in liver and intestinal mucosal cells. Apolipoproteins exists in several divisions, including the B Apolipoproteins (ApoB). ApoB48, which contains 2,152 amino acids, is required for chylomicron formation in the intestine. L. Chan (1992) J. Biol. Chem. 267, 25621–25624.

ApoB100, which contains 4,536 amino acids, is required for assembly of VLDL in the liver. M. M. Veniant, V. Pierotti, D. Newland, C. M. Cham, D. A. Sanan, R. L. Walzem (1997) J. Clin. Invest. 100, 180–188. Other variants of apoB include apoB23, apoB36, and apoB53. J. Kruezer, A. L. White, T. J. Knott, M- L. Jien, M. Mehrabian, J. Scott, S. G. Young, and M. E. Haberland (1997) J. Lip. Res. 38, 324–342. The amino-terminal sequences of apoB tend to be conserved.

SUMMARY OF THE INVENTION

The subject invention provides a method for inhibiting the binding of low density lipoprotein to blood vessel matrix in a subject, comprising administering to the subject an effective amount of a substance capable of binding to the amino-terminal region of apolipoprotein B, thereby inhibiting the binding of low density lipoprotein to blood vessel matrix.

This invention also provides a method of treating atherosclerosis in a subject, comprising administering to the subject an effective amount of a substance capable of binding to the amino-terminal region of apolipoprotein B, thereby treating the atherosclerosis.

This invention also provides a method for inhibiting the binding of low density lipoprotein to blood vessel matrix in a subject, comprising administering to the subject an effective amount of a substance capable of competing with the amino-terminal region of apolipoprotein B for binding to blood vessel matrix, thereby inhibiting the binding of low density lipoprotein to blood vessel matrix.

This invention further provides a method of treating atherosclerosis in a subject, comprising administering to the subject an effective amount of a substance capable of competing with the amino-terminal region of apolipoprotein B for binding to blood vessel matrix, thereby treating the atherosclerosis.

This invention also provides a method for identifying a compound capable of ameliorating atherosclerosis, comprising: (a) contacting the compound with the amino-terminal region of apolipoprotein B under conditions permitting binding between the compound and the amino-terminal region of apolipoprotein B; (b) detecting specific binding of the compound to the amino-terminal region of apolipoprotein B; and (c) identifying the compound that specifically binds to the amino-terminal region of apolipoprotein B, thereby identifying a compound capable of ameliorating atherosclerosis.

Additionally, this invention provides a kit for inhibiting the binding of low density lipoprotein to blood vessel matrix, wherein the kit comprises a substance capable of binding to the amino-terminal region of apolipoprotein B.

This invention further provides a kit for inhibiting the binding of low density lipoprotein to blood vessel matrix, wherein the kit comprises a polypeptide sharing a sequence of at least 6 amino acids, or analogs thereof, with the amino-terminal region of apolipoprotein B. Additionally, this invention provides a mutant nonhuman organism that overproduces the amino-terminal region of apolipoprotein B.

DETAILED DESCRIPTION OF THE INVENTION

Apolipoprotein B:

ApoB is the major protein present on plasma lipoproteins LDL, VLDL and chylomicrons. LDL and VLDL contain full-length apoB (B100), whereas chylomicrons contain the amino terminal 48% of the apoB (B48). The complete apoB sequence has been determined (Cladaras et al 1986, EMBO J Vol 5, p3495). Different regions of apoB have been shown to have different functions including binding to LDL receptor and lipids. It was shown that the amino (N) terminal region of apoB (NTAB) can interact with lipase and others have shown that it can interact with macrophage scavenger receptor.

Lipoprotein retention in the blood vessel matrix is considered as a major event in the development of atherosclerosis and we propose that NTAB is the major determinant in mediating LDL binding to different matrix components. Using isolated fragments and antibodies to different regions of apoB, it was shown that domains in the amino terminal 17% of apoB (B17) mediate LDL binding to vessel matrix. B17 has the following amino acid sequence:

MDPPRPALLALLALPALLLLLLAGAR-
AEEEMLENVSLVCPKDATRFKHLRKYTYN
YEAESSSGVPGTADSRSATRINCK-
VELEVPQLCSFILKTSQCTLKEVYGFNPEGK
ALLKKTKNSEEFAAAM-
SRYELKLAIPEGKQVFLYPEKDEPTY-
ILNIKRGIISALL VPPETEEAKQVLFLDTVYGNC-
STHFTVKTRKGNVATEISTERDLGQCDRFKPIRT
GISPLALIKGMTRPLSTLISSSQSC-
QYTLDAKRKHVAEAICKEQHLFLPFSYNNK YGM-
VAQVTQTLKLEDTPKINSRFFGEGTKK-
MGLAFESTKSTSPPKQAEAVLKTLQ
ELKKLTISEQNIQRANLFNKLVTELR-
GLSDEAVTSLLPQLIEVSSPITLQALVQC GQPQC-
STHILQWLKRVHANPLLIDVVTYLVAL-
IPEPSAQQLREIFNMARDQRSRA
TLYALSHAVNNYHKTNPTGTQELL-
DIANYLMEQIQDDCTGDEDYTYLILRVIGNM GQT-
MEQLTPELKSSILKCVQSTKPSLMIQ-
KAAIQALRKMEPKDKDQEVLLQTFLD
DASPGDKRLAAYLMLMRSPSQADINKIV-
QILPWEQNEQVKNFVASHIANILNSEE
LDIQDLKKLVKEALKESQLPTVMDFRKF-
SRNYQLYKSVSLPSLDPASAKIEGNLI FDPNNYLP-
KESMLKTTLTAFGFASADLIEIGLEGKG-
FEPTLEALFGKQGFFPDSV
NKALYWVNGQVPDGVSKVLVDHFGYTKD-
DKHEQDMVNGIMLSVEKLIKDLKSKEV PEARAY-
LRILGEELGFASLHDLQLLGKLLLMGARTLQGI

This sequence provides a genetic target to screen individuals at risk for atherosclerosis. This sequence further provides a biochemical target to block the accumulation of LDLs and, thereby, prevent the occurrence of atherosclerosis.

In addition to naturally-occurring forms of polypeptides derived from NTAB, the present invention also embraces other NTAB polypeptides such as polypeptide analogs of NTAB. Such chemical analogs include fragments of NTAB. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of the NTAB polypeptide. Such products share at least one of the biological properties of NTAB but may differ in others.

As examples, products of the invention include those which are foreshortened by e.g., deletions; or those which are more stable to hydrolysis (and, therefore, may have more pronounced or longerlasting effects than naturally-occurring products); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within NTAB, which fragments may possess one property of NTAB and not others. It is noteworthy that activity is not necessary for any one or more of the polypeptides of the invention to have therapeutic utility or utility in other contexts, such as in assays of NTAB antagonism. Competitive antagonists may be quite useful in, for example, cases of overproduction of NTAB.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., Cell, 23, 309–310 (1981); Ross et al., Nature, 294, 654–658 (1981); Walter et al., Proc. Natl. Acad. Sci. USA ,78, 4882–4886 (1981); Wong et al., Proc. Natl. Sci. USA, 79, 5322–5326 (1982); Baron et al., Cell, 28, 395–404 (1982); Dressman et al., Nature, 295, 185–160 (1982); and Lerner, Scientific American, 248, 66–74 (1983). See also, Kaiser et al. [Science, 223, 249–255 (1984)] relating to biological and immunological properties of synthetic peptides which approximately share secondary structures of peptide hormones but may not share their primary structural conformation. These studies show that chemical analogs of NTAB share secondary structual features that make them potentially valuable as competitive inhibitors of LDL binding to subendothelial matrix.

Other chemical analogs of NTAB include peptidomimetic compounds which may be at least partially unnatural. The peptidomimetic compound may be a small molecule mimic of a portion of the amino acid sequence of NTAB. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared. The compound of the present invention may include L-,D- or unnatural amino acids, alpha, alpha- disubstituted amino acids, N-alkyl amino acids, lactic acid (an isoelectronic analog of alanine). The peptide backbone of the compound may have at least one bond replaced with PSI-[CH=CH]. The compound may further include trifluorotyrosine, p-Cl-phenylalanine, p-Br-phenylalanine, poly-L-propargylglycine, poly-D,L-allyl glycine, or poly-L-allyl glycine.

Additionally, the peptidomimetic may have a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline.

The subject invention provides a method for inhibiting the binding of low density lipoprotein to blood vessel matrix in a subject, comprising administering to the subject an effective amount of a substance capable of binding to the amino-terminal region of apolipoprotein B, thereby inhibiting the binding of low density lipoprotein to blood vessel matrix.

Figure 1:
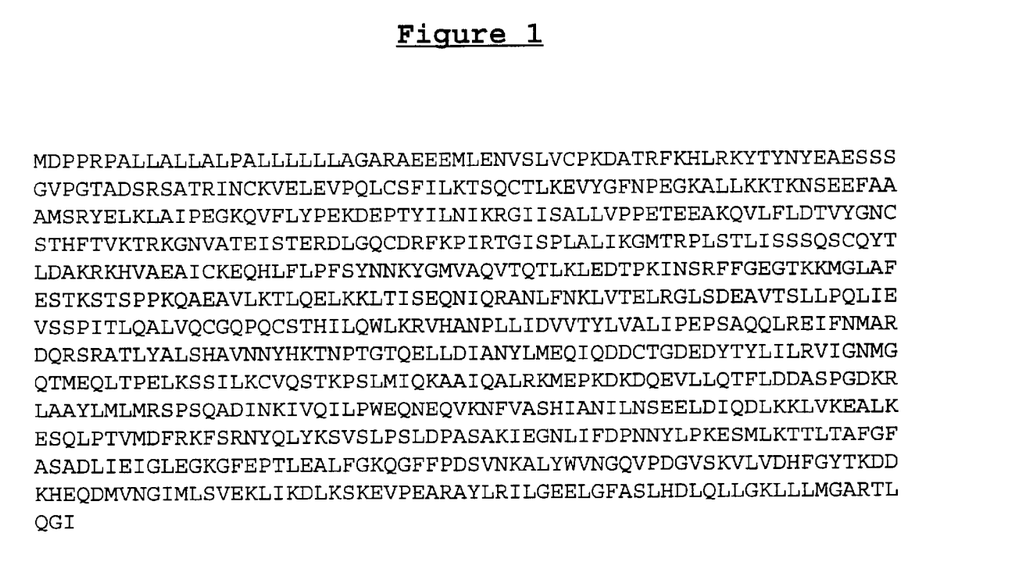
FIG. 1 Amino acid sequence of apolipoprotein B17 (an amino-terminal fragment of apolipoprotein B).

As used herein, the "amino-terminal region of apolipoprotein B" includes sequence shown in FIG. 1. (SEQ. ID NO. 1) The "amino-terminal region of apolipoprotein B" also includes the sequence in FIG. 1 wherein amino have been added, deleted or substituted. In an embodiment, the substitutions replace amino acids with other amino acids having similar chemical properties. For example, Valine may be substituted for Leuline. This invention also contemplates using chemical analogs of amino acids. (See previous discussion herein of chemical analogs.)

Further in the practice of this invention, the "administering" may be effected or performed using any of the various methods known to those skilled in the art. In one embodiment, the administering comprises administering intravenously. In another embodiment, the administering comprises administering intramuscularly. In yet another embodiment, the administering comprises administering subcutaneously.

This invention also provides a method of treating atherosclerosis in a subject, comprising administering to the subject an effective amount of a substance capable of binding to the amino-terminal region of apolipoprotein B, thereby treating the atherosclerosis.

In an embodiment of the above-described methods, the amino-terminal region of apolipoprotein B comprises substantially the same sequence as the amino acid sequence shown in FIG. 1.

In another embodiment of the above-described methods, the substance is an antibody or a fragment thereof.

The fragment of the antibody has binding affinity similar to the antibody. In an embodiment, the fragment of the antibody is produced by proteolytic digestion of the antibody.

In a different embodiment of the above-described methods, the substance is a monoclonal antibody or a fragment thereof.

This invention also provides a method for inhibiting the binding of low density lipoprotein to blood vessel matrix in a subject, comprising administering to the subject an effective amount of a substance capable of competing with the amino-terminal region of apolipoprotein B for binding to blood vessel matrix, thereby inhibiting the binding of low density lipoprotein to blood vessel matrix.

This invention further provides a method of treating atherosclerosis in a subject, comprising administering to the subject an effective amount of a substance capable of competing with the amino-terminal region of apolipoprotein B for binding to blood vessel matrix, thereby treating the atherosclerosis.

In an embodiment of the above-described methods, the substance is the amino-terminal region of apolipoprotein B.

In another embodiment of the above-described methods, the substance is a portion of the amino-terminal region of apolipoprotein B.

The amino-terminal region of apolipoprotein B of is shown in FIG. 1. As used herein, "a portion of the amino-terminal region of apolipoprotein B" represents a sufficient part of the amino-terminal region of apolipoprotein B to share secondary structural features with the sequence shown in FIG. 1. Such sequences would be recognized by those skilled in the art.

In a different embodiment of the above-described methods, the substance is an amino-terminal fragment of apolipoprotein B designated B17.

As used herein a "fragment of apolipoprotein B designated B17" is a fragment that represents approximately the 17% amino-terminal-most portion of apolipoprotein B.

In yet another embodiment of the above-described methods, the substance comprises a portion of the amino-terminal fragment of apolipoprotein B designated B17.

As used herein, "a portion of the amino-terminal fragment of apolipoprotein B designated B17" a sufficient part of the amino-terminal region of apolipoprotein B to share secondary structural features with the 17% amino-terminal portion of apolipoprotein B.

In still another embodiment of the above-described methods, the substance comprises a chemical analog of the amino-terminal region of apolipoprotein B.

Chemical analogs were described previously described herein.

This invention also provides a method for identifying a compound capable of ameliorating atherosclerosis, comprising: (a) contacting the compound with the amino-terminal region of apolipoprotein B under conditions permitting binding between the compound and the amino-terminal region of apolipoprotein B; (b) detecting specific binding of the compound to the amino-terminal region of apolipoprotein B; and (c) identifying the compound that specifically binds to the amino-terminal region of apolipoprotein B, thereby identifying a compound capable of ameliorating atherosclerosis.

This invention also provides the above-described methods, wherein the compounds are not previously known.

This invention further provides the compounds identified by the above-described methods.

Additionally, this invention provides a method for ameliorating atherosclerosis in a subject comprising administering to the subject an amount of the compounds identified by the above-described methods effective to ameliorate atherosclerosis.

The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. Variants of the amino-terminal region of apolipoprotein B with a lower affinity for blood vessel matrix will require lower dosages than variants of amino-terminal region of apolipoprotein B with higher affinity for blood vessel matrix. One of skill in the art could routinely perform empirical activity tests to determine the bioactivity in bioassays and thus determine the effective amount.

This invention also provides a pharmaceutical composition comprising an amount of the above-described compounds effective to ameliorate atherosclerosis and a pharmaceutically acceptable carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

Additionally, this invention provides a kit for inhibiting the binding of low density lipoprotein to blood vessel matrix, wherein the kit comprises a substance capable of binding to the amino-terminal region of apolipoprotein B In an embodiment, the substance in the above-described kit is an antibody or a fragment thereof.

This invention further provides a kit for inhibiting the binding of low density lipoprotein to blood vessel matrix, wherein the kit comprises a polypeptide sharing a sequence of at least 6 amino acids, or analogs thereof, with the amino-terminal region of apolipoprotein B.

In an embodiment, sequences of at least 6 amino acids are selected by choosing amino acids that are part of antigenic determinants or other prominent secondary structural features. In a further embodiment, the sequence of 6 amino acids is chosen to overlap the antigenic determinant for the monoclonal antibody designated M17. In another embodiment, the sequence of 6 amino acids is chosen to include a portion of the amino-terminal region of apolipoprotein B that contains a proline.

The mutant nonhuman organism may be produced by generation of a transgenic nonhuman organism which has exogenous DNA encoding the amino-terminal region of apolipoprotein B. In an embodiment, the amino-terminal region of apolipoprotein B is B17.

Additionally, this invention provides a mutant nonhuman organism that overproduces the amino-terminal region of apolipoprotein B.

This invention will be better understood from the examples which follow. However, one skilled in the art will readily appreciate that the specific methods and results discussed are merely illustrative of the invention as described more fully in the claims which follow thereafter.

Experimental Details:

Materials:

Preparation of B17:

ApoB17 was cloned and expressed using a recombinant adeno virus in 293 kidney cells. Cells were incubated with control or B17 containing adeno viruses for 36 hours in DMEM medium containing 2% serum. The virus-containing medium was then removed, and DMEM medium containing 1.5% BSA was added to the cells and incubation was continued for eight hours. During this time B17 was secreted into medium by cells incubated with B17 containing virus but not by control virus. Control and B17 media were collected and filtered. LDL was incubated in these media to assess the binding to matrix or matrix proteins.

Antibodies:

Monoclonal antibody M19 recognizes the amino terminal region of apoB whereas monoclonal antibody M47 recognizes the C-terminal region of apoB (Pillarisetti, et al. 1994 J. Biol. Chem Vol. 269:949).

Preparation of vascular matrix:

Normal vascular matrix is composed of several proteins including collagen, laminin, fibronectin and proteoglycans (heparin+heparan, chondroitin and dermatan sulfates). One or more of these proteins may mediate LDL binding to the blood vessel matrix. In vivo this matrix is synthesized by endothelial cells, smooth muscle cells or macrophages. For our in vitro experiments we used a matrix synthesized by endothelial cells. Endothelial cells from bovine aorta and cultured as previously described. (Pillarisetti et al. 1992. Identification of a heparin-releasable lipoprotein lipase binding protein from endothelial cells. *J. Biol. Chem.* 267: 16517–16522). Briefly cells were grown to confluency in minimal essential medium (MEM) containing 10% fetal bovine serum (FBS). On the day of experiment cells were gently lifted by incubation with saline containing 0.1% Triton X-100+20 mM $NH_4OH$ for 5–10 min. This procedure, as others have shown, removes cells leaving the matrix intact. This matrix contains the above mentioned matrix proteins. LDL binding to this matrix was studied in the presence and absence of B17 or antibodies.

Individual matrix components:

In some experiments, purified and commercially available matrix proteins were used. Collagen, laminin and fibronectin were from Sigma Chemical Co. A gel containing heparin (heparin-Sepharose) was from Pharmacia. Chondroitin sulfate proteoglycan was from Becton and Dickinson. Plastic plates were coated with these proteins and LDL binding to coated plates was studied in the presence and absence of intervening agents.

Blood vessels:

Animal (Golden Syrian Hamster) preparation for injecting LDL into blood vessels was described in detail previously (Rutledge et al Circulation Res. 1997, Vol 80, p819). LDL was injected in the presence or absence of apoB antibodies.

Labeled LDL:

LDL (d<1.063) was isolated from human plasma using density gradient ultracentrifugation. LDL was either radiolabeled with $^{125}$Iodine or fluorescent labeled with DiI.

Determining LDL binding:

Two types of experiments were carried out. First, as a model of glycosaminoglycan interaction, LDL binding to heparin Sepharose was performed. Affinity was determined by elution with a step-wise gradient of NaCl. Second, labeled LDL was incubated in medium containing 3% albumin with vascular matrix or with purified matrix components (as above) for 1 h at 37° C. Unbound LDL was removed and bound LDL was assessed by releasing with 0.1N NaOH.

Experiments:

NTAB Has a Higher Affinity for Heparin Than for LDL

Figure 2:
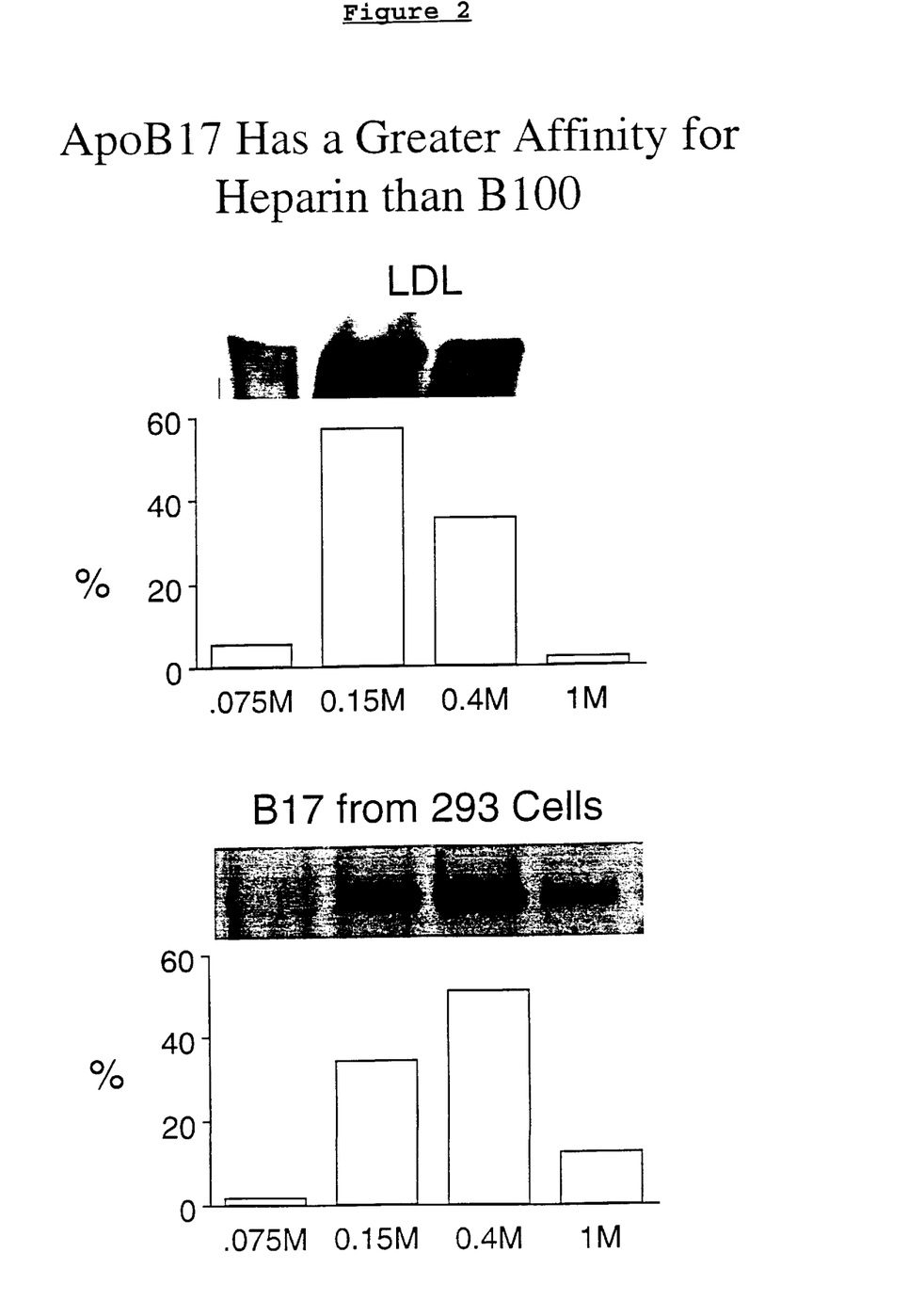
FIG. 2 Bar graph comparing LDL's binding affinity for heparin with ApoB17's binding affinity for heparin.

Heparin-Sepharose chromatography was performed on LDL and ApoB17. Eluted apoB was identified by immunoblotting with a polyclonal apoB antibody. A major portion of bound LDL (~60% of total loaded) was eluted at physiological salt concentration, i.e. 0.15M NaCl. (See FIG. 2.) In different experiments about 20–40% of bound LDL was eluted at 0.4M NaCl. Some of B17 was also eluted with 0.15M NaCl. A major peak, however, was eluted at 0.4M NaCl. In addition, 15–20% of bound apoB17 was also eluted at 1.0M NaCl. These data show that NTAB has GAG binding regions and has a higher affinity for heparin than LDL.

ApoB 48's Affinity for Heparin is Greater than AnoB 100's Affinity for Heparin

Figure 3:
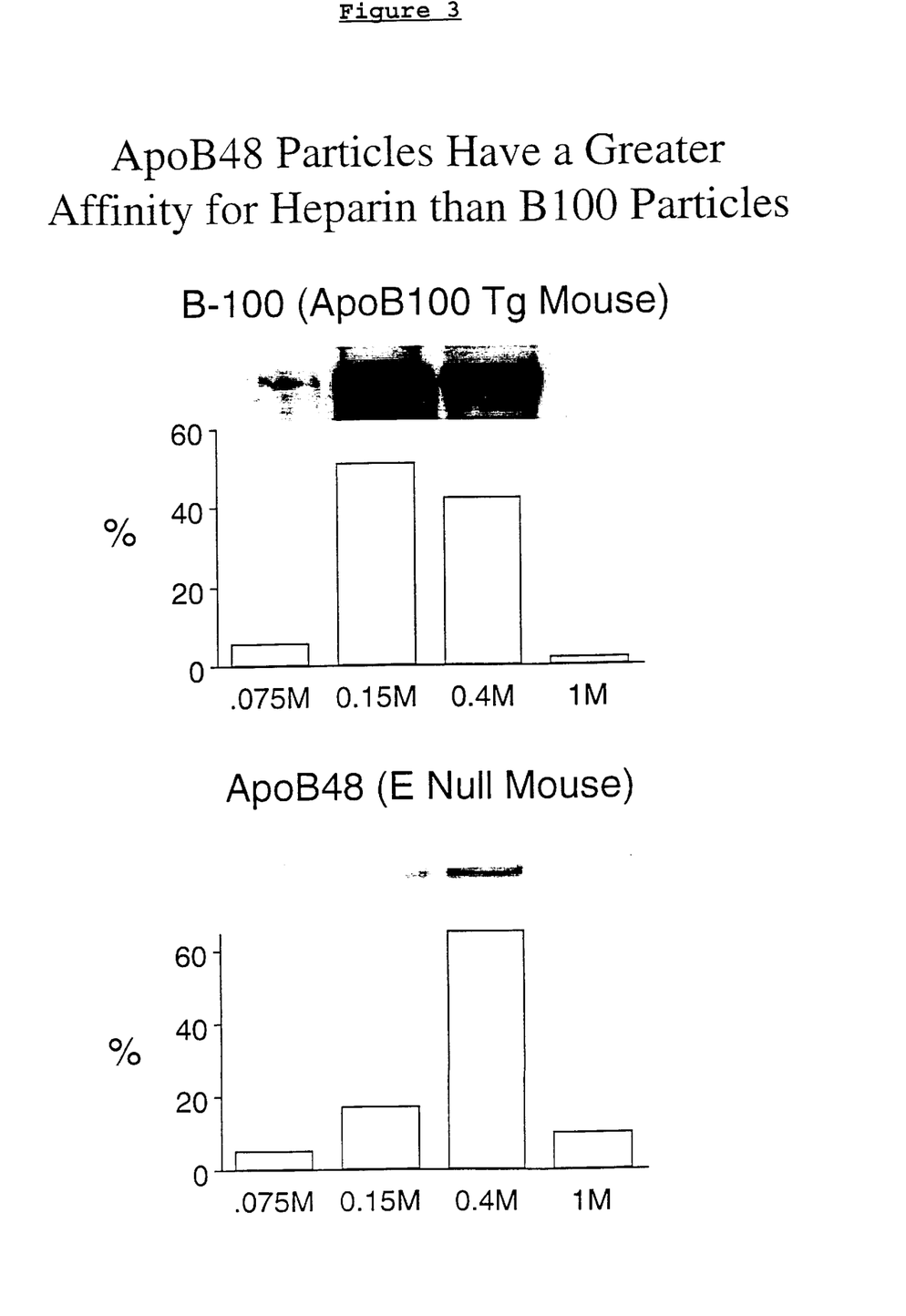
FIG. 3 Bar graph comparing ApoB48's binding affinity for heparin with ApoB100's binding affinity for heparin.

ApoB 100 particles were isolated from mice that overexpresses human B100. ApoB 48 particles were isolated from apoE null mice. By western blot analysis we confirmed that neither B100 nor B48 particles carried apoE. Like in the pervious experiment, most of the bound LDL eluted at 0.15 and some in 0.4M NaCl buffers. (See FIG. 3.) In contraction, about 70% of bound B48 was eluted at 0.4M NaCl. This shows that even when NTAB is present as a part of a lipid particle it still has a higher affinity for GAG.

NTAB is an Important Mediator of LDL Binding to Heparin

Figure 4:
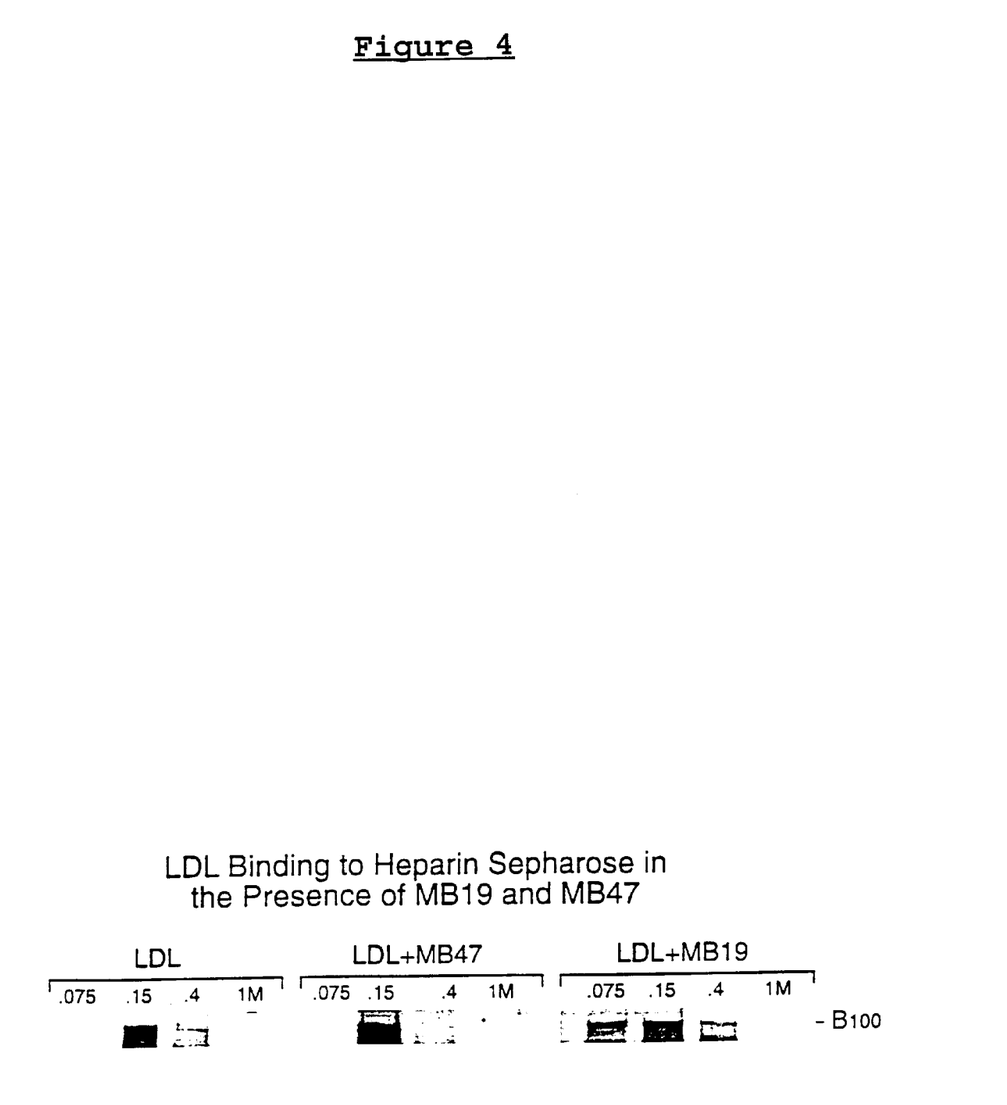
FIG. 4 Bar graph comparing M19's effect on LDL binding to heparin with M47's effect on LDL binding to heparin.

To further show that LDL binding to heparin is mediated by NTAB, Heparin-Sepharose chromatography of LDL was performed in the presence and absence of apoB antibodies. ApoB eluting at difference salt concentrations was identified by immunoblotting. In the absence of any antibodies most of the LDL was eluted at 0.15M NaCl. Addition of M47 did not affect this binding and most LDL still eluted at 0.15M NaCl. (See FIG. 4.) However, when M19 was used a portion of apoB did not bind and eluted in the unbound fraction (i.e. 0.075M). Thus, blocking the NTAB in LDL inhibits LDL's interaction with heparin.

NTAB is an Important Mediator of LDL Binding to Matrix

Figure 5:
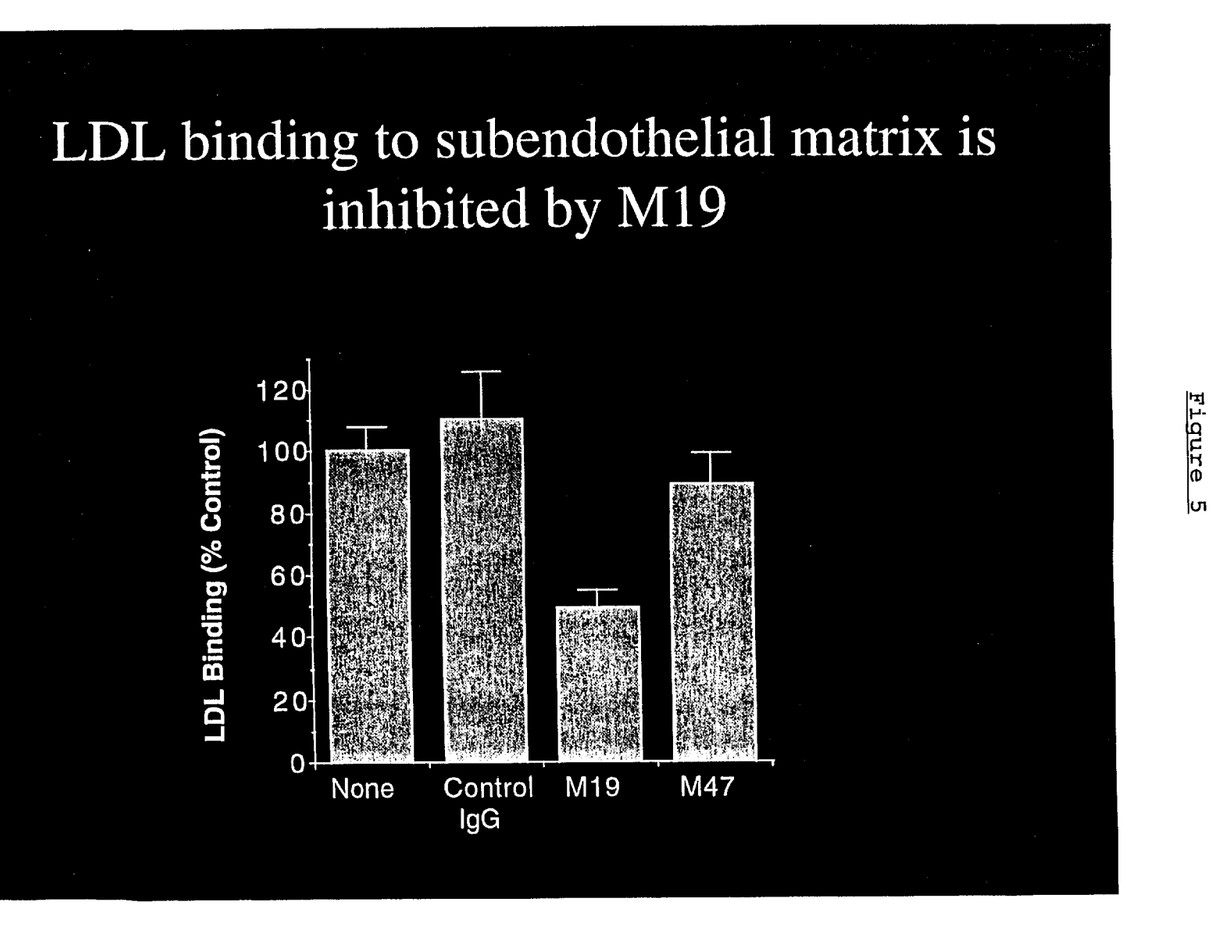
FIG. 5 Bar graph comparing M19's effect on LDL binding to subendothelial matrix with M47's effect on LDL binding to subendothelial matrix.

Incubation in the presence of a control IgG did not affect LDL binding to matrix. M19 inhibited LDL binding to matrix by about 50%. (See FIG. 5.) In contrast, M47 inhibited LDL binding by only 10%. Again showing that the amino-terminal region of apoB mediates LDL binding to matrix.

NTAB is an Important Mediator of LDL Binding to Matrix Components

Figure 6:
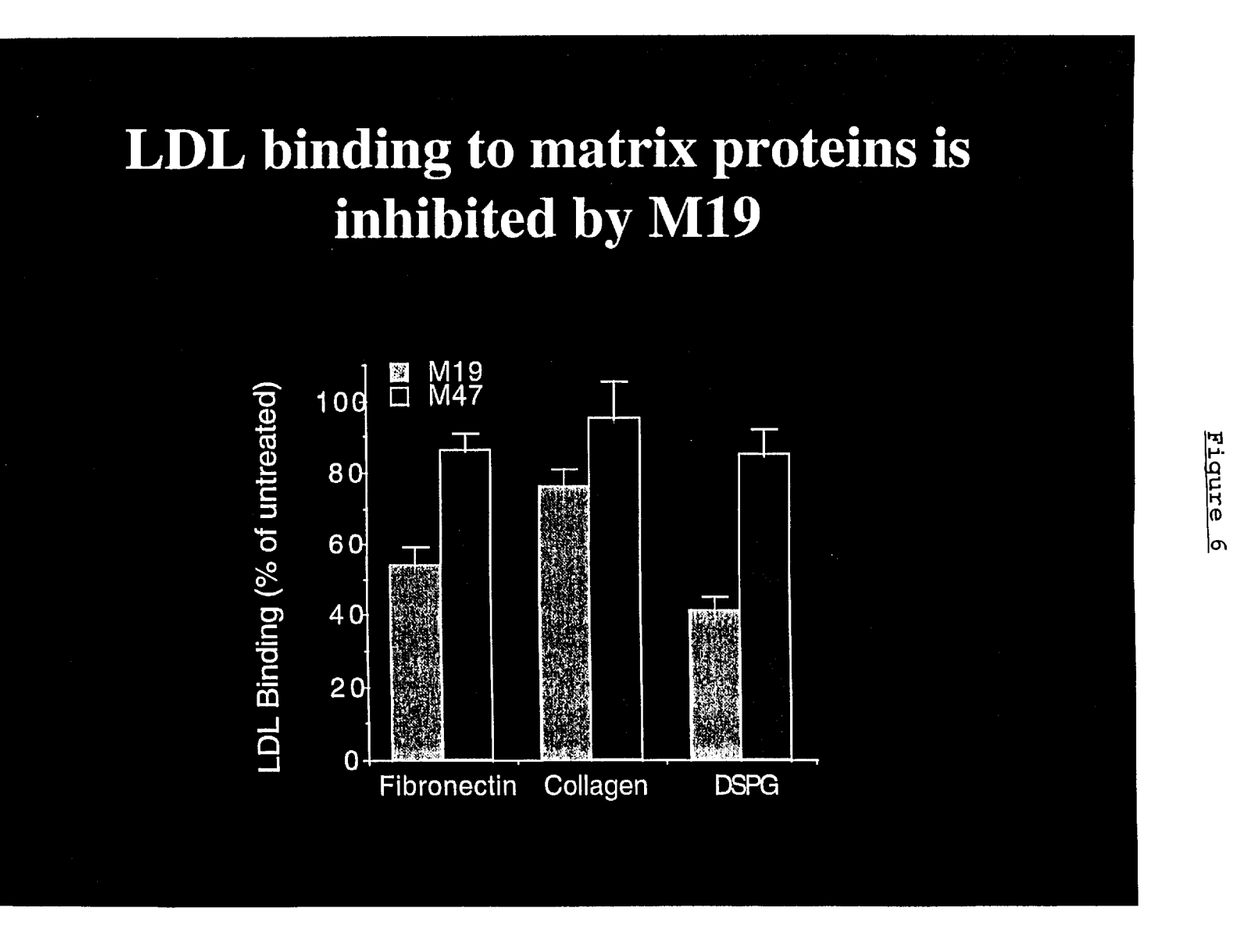
FIG. 6 Bar graph comparing M19's effect on LDL binding to matrix proteins with M47's effect on LDL binding to matrix proteins.

Plates coated with different matrix components were incubated with LDL in the presence of apoB antibodies. M19 again inhibited LDL binding. LDL binding to: fibronectin was inhibited by 48%, to collagen by 23%, and to DSPG by 52%. In contrast, M47 inhibited different bindings by only 10–15%. (See FIG. 6.) (These values represent % of values obtained for control incubations that did not receive antibodies.) These data show that NTAB is an important mediator of LDL binding to matrix proteins and proteoglycans.

A Soluble Fragment of NTAB Inhibits LDL Binding to Matrix

Figure 7:
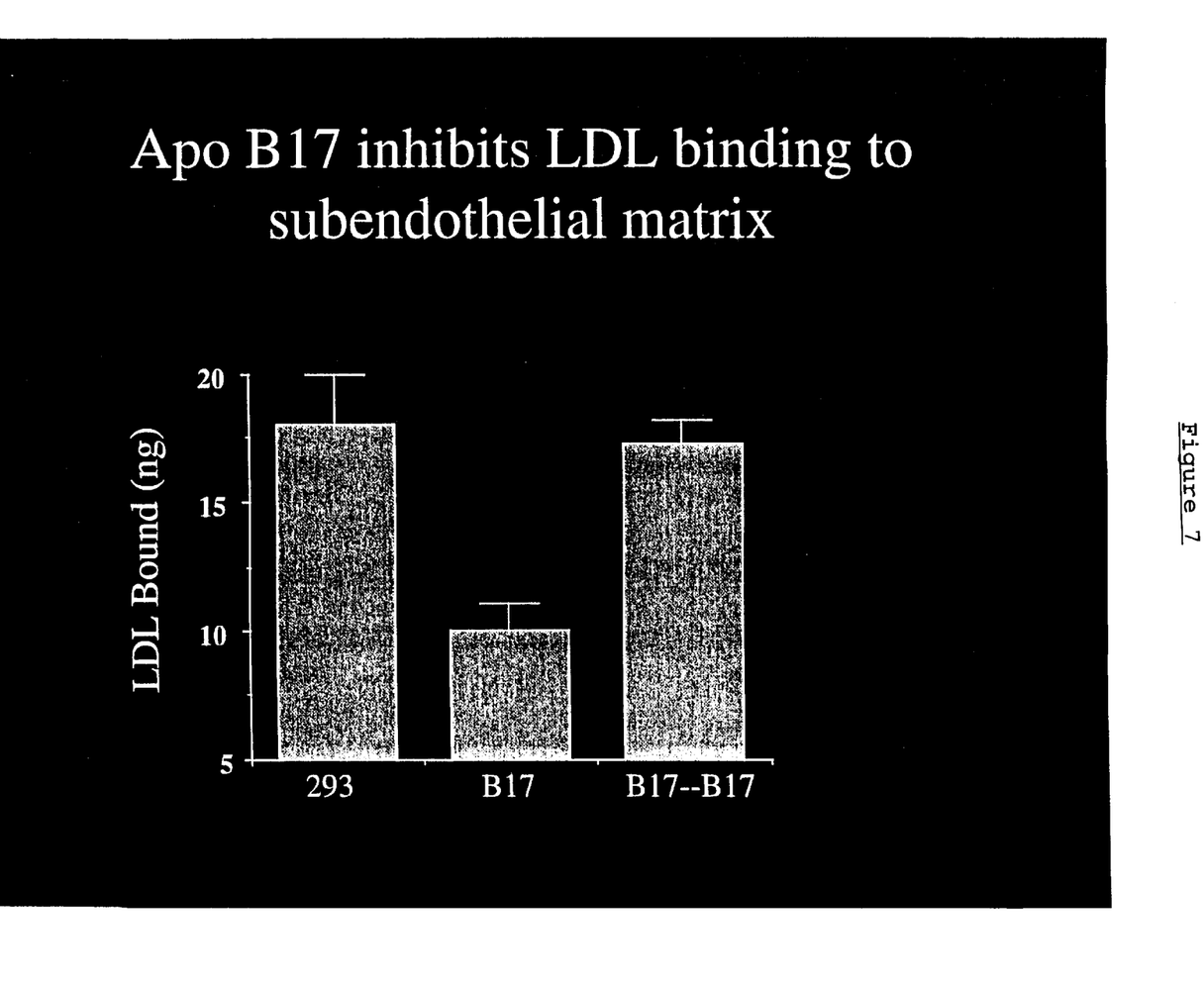
FIG. 7 Bar graph showing the effect of ApoB17 on LDL binding to subendothelial matrix.

LDL was allowed to bind to matrix in the presence of media from control virus transfected 293 cells or B17 virus cells. ApoB17 inhibited LDL binding to matrix by 42%. (See FIG. 7.) To determine if this inhibition is due to apoB17, B17 was removed by immunoprecipitation and the media was then used to inhibit LDL binding. The inhibitory effect of B17 was abolished when B17 was specifically removed.

A Soluble Fragment of NTAB Matrix-Bound LDL

Figure 8:
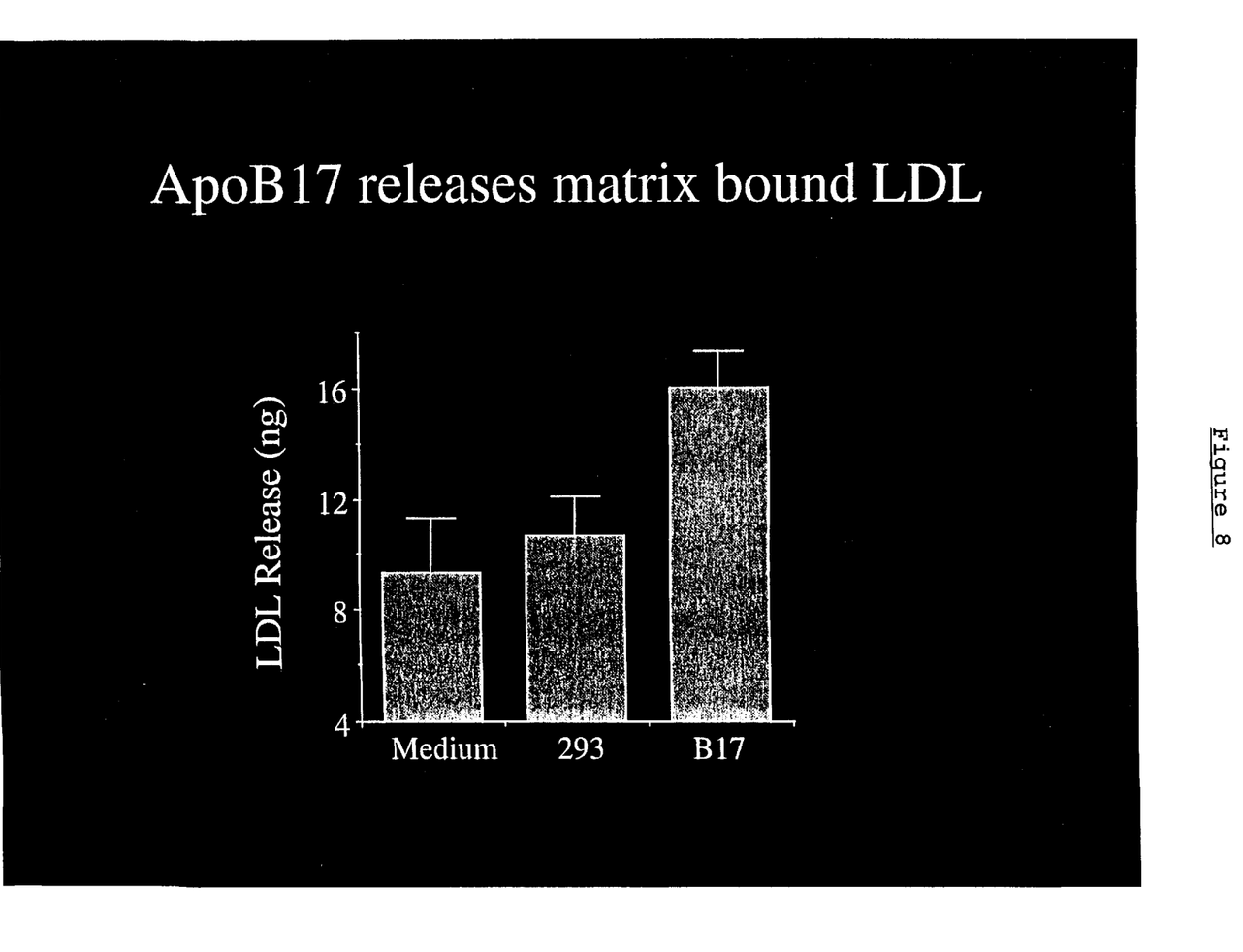
FIG. 8 Bar graph showing that ApoB17 releases matrix bound LDL.
Figure 9:
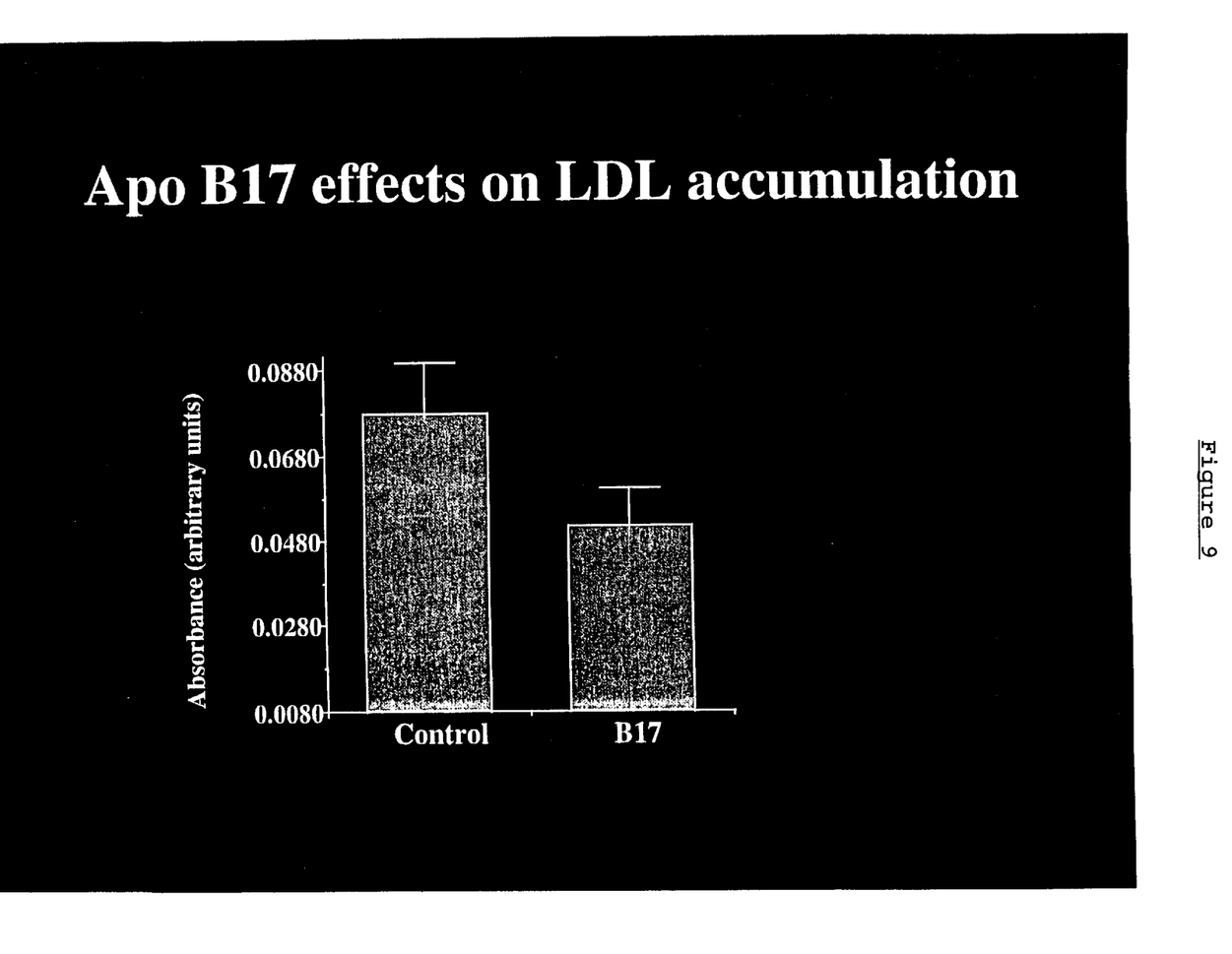
FIG. 9 Bar graph showing the effect of ApoB17 on LDL accumulation.

We next tested for B17's ability to release matrix bound LDL. (See FIG. 8.) In this experiment LDL was first bound to matrix and then incubated with control or B17 media. Compared to control medium or 293 conditioned media, B17 conditioned medium released ~1.7 fold more LDL into the medium. (See FIG. 9.)

In Vivo Effects of Overexpression of apoB17 on Atherosclerosis Development

An adenovirus producing apoB17 in mice was produced. This virus led to detectable amounts of apoB17 in the plasma for more than 30 days after injection of the virus into mice. Three atherosclerosis prone apoE knock out mice received the virus and another three received a control virus. ApoB17 was found in the bloodstream and most of this apoB17 was not associated with circulating lipoproteins. At age 12 weeks, four week after viral injection, the mice were sacrificed and atherosclerosis in the aortic root was quantified. The B17 mice had approximately half the amount of atherosclerosis as the control group (166,000 versus 382,000 um of atherosclerosis). This pilot study suggests that NTAB will be anti-atherogenic.

Further Characterization of the Atherogenic Region of ApoB

In order to more precisely localize the atherogenic regions of apoB, we have constructed a plasmid that produces apoB7, the amino-terminal 7% of apoB. By expressing these and similar constructs containing different fragments of the amino-terminal region of apoB, it will be possible to identify even more precisely the atherogenic region of apoB. Further, by mutating this region, we may render apoB non-atherogenic.

Summary of Results:

$^{125}$I-LDL binding to matrix was inhibited, by approximately 50%, by monoclonal antibody MB19 that recognizes the amino-terminus of apoB, but not by MB47 that recognizes the C-terminus of apoB.

LDL binding was also inhibited by B17 but not control medium. The inhibition caused by B17 was lost following removal of B17 from medium by immunoprecipitation with apoB antibodies.

M19 but not M47 inhibited LDL binding to different matrix components. To chondroitin sulfate by 42%, to heparin by 43% and to laminin by 23%.

$^{125}$LDL binding to heparin-Sepharose was also inhibited by M19.

LDL binding to blood vessel was inhibited, by >50%, by M19 but not by M47.

Conclusions:

These data show that LDL can interact with different matrix components and NTAB is a significant mediator of these interactions. In particular, our studies show that the amino-terminal region of apoB is an important mediator of LDL binding to the subendothelial matrix of blood vessels. Finally, it is concluded that the NTAB, which is thought to extend away from the core of LDL, causes LDL to accumulate in arteries.

What is claimed is:

1. A method for inhibiting the binding of low density lipoprotein to blood vessel matrix in a subject, comprising administering to the subject an effective amount of a substance capable of binding to the amino-terminal region of apolipoprotein B, thereby inhibiting the binding of low density lipoprotein to blood vessel matrix.

2. The method of claim 1, wherein the amino-terminal region of apolipoprotein B comprises substantially the same sequence as the amino acid sequence shown in FIG. 1.

3. The method of claim 1, wherein the substance is an antibody or a fragment thereof.

4. The method of claim 1, wherein the substance is a monoclonal antibody or a fragment thereof.

5. A method of preventing atherosclerosis in a subject, comprising administering to the subject an effective amount of a substance capable of binding to the amino-terminal region of apolipoprotein B, thereby preventing the atherosclerosis.

6. A method for preventing atherosclerosis in a subject comprising administering to the subject an amount of an antibody which recognizes the amino terminal region of apolipoprotein B (apoB) effective to prevent atherosclerosis.

7. A kit for inhibiting the binding of low density lipoprotein to blood vessel matrix, wherein the kit comprises a substance which specifically binds to the amino-terminus region of apolipoprotein B.

8. The kit of claim 7, wherein the substance is an antibody or a fragment thereof.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 809 amino acids
      (B) TYPE: amino acid
      (C) STRANDEDNESS:
      (D) TOPOLOGY: linear    (ii) MOLECULE TYPE: peptide    (xi) SEQUENCE DESCRIPTION: SEQ ID NO:1:

```
Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
            35                  40                  45

Leu Arg Lys Tyr Thr Tyr Asn Tyr Glu Ala Glu Ser Ser Ser Gly Val
        50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
            100                 105                 110

Leu Lys Lys Thr Lys Asn Ser Glu Glu Phe Ala Ala Met Ser Arg
        115                 120                 125

Tyr Glu Leu Lys Leu Ala Ile Pro Glu Gly Lys Gln Val Phe Leu Tyr
        130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Asn Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320
```

-continued

Gln Ala Glu Ala Val Leu Lys Thr Leu Gln Glu Leu Lys Lys Leu Thr
                    325                 330                 335

Ile Ser Glu Gln Asn Ile Gln Arg Ala Asn Leu Phe Asn Lys Leu Val
                    340                 345                 350

Thr Glu Leu Arg Gly Leu Ser Asp Glu Ala Val Thr Ser Leu Leu Pro
                    355                 360                 365

Gln Leu Ile Glu Val Ser Ser Pro Ile Thr Leu Gln Ala Leu Val Gln
                    370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                    405                 410                 415

Leu Ile Pro Glu Pro Ser Ala Gln Gln Leu Arg Glu Ile Phe Asn Met
                    420                 425                 430

Ala Arg Asp Gln Arg Ser Arg Ala Thr Leu Tyr Ala Leu Ser His Ala
                    435                 440                 445

Val Asn Asn Tyr His Lys Thr Asn Pro Thr Gly Thr Gln Glu Leu Leu
                    450                 455                 460

Asp Ile Ala Asn Tyr Leu Met Glu Gln Ile Gln Asp Cys Thr Gly
465                 470                 475                 480

Asp Glu Asp Tyr Thr Tyr Leu Ile Leu Arg Val Ile Gly Asn Met Gly
                    485                 490                 495

Gln Thr Met Glu Gln Leu Thr Pro Glu Leu Lys Ser Ser Ile Leu Lys
                    500                 505                 510

Cys Val Gln Ser Thr Lys Pro Ser Leu Met Ile Gln Lys Ala Ala Ile
                    515                 520                 525

Gln Ala Leu Arg Lys Met Glu Pro Lys Asp Lys Asp Gln Glu Val Leu
                    530                 535                 540

Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                    565                 570                 575

Ile Val Gln Ile Leu Pro Trp Glu Gln Asn Glu Gln Val Lys Asn Phe
                    580                 585                 590

Val Ala Ser His Ile Ala Asn Ile Leu Asn Ser Glu Glu Leu Asp Ile
                    595                 600                 605

Gln Asp Leu Lys Lys Leu Val Lys Glu Ala Leu Lys Glu Ser Gln Leu
                    610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                    645                 650                 655

Gly Asn Leu Ile Phe Asp Pro Asn Asn Tyr Leu Pro Lys Glu Ser Met
                    660                 665                 670

Leu Lys Thr Thr Leu Thr Ala Phe Gly Phe Ala Ser Ala Asp Leu Ile
                    675                 680                 685

Glu Ile Gly Leu Glu Gly Lys Gly Phe Glu Pro Thr Leu Glu Ala Leu
                    690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                    725                 730                 735

-continued

```
His Phe Gly Tyr Thr Lys Asp Asp Lys His Glu Gln Asp Met Val Asn
            740             745                 750

Gly Ile Met Leu Ser Val Glu Lys Leu Ile Lys Asp Leu Lys Ser Lys
        755             760             765

Glu Val Pro Glu Ala Arg Ala Tyr Leu Arg Ile Leu Gly Glu Glu Leu
    770             775             780

Gly Phe Ala Ser Leu His Asp Leu Gln Leu Leu Gly Lys Leu Leu Leu
785                 790             795                 800

Met Gly Ala Arg Thr Leu Gln Gly Ile
                805
```